United States Patent

Henry et al.

(10) Patent No.: US 7,913,689 B2
(45) Date of Patent: Mar. 29, 2011

(54) IDENTIFICATION SYSTEM AND METHOD FOR MASK AND VENTILATOR COMPONENTS

(75) Inventors: Robert Edward Henry, Roseville (AU); Karthikeyan Selvarajan, Gosford (AU); Philip Rodney Kwok, Chatswood (AU); Philip John Gunning, North Rocks (AU); John David Oates, Stanhope Gardens (AU)

(73) Assignee: Resmed Limited, Bella Vista, New South Wales (AU)

( * ) Notice: Subject to any disclaimer, the term of this patent is extended or adjusted under 35 U.S.C. 154(b) by 1127 days.

(21) Appl. No.: 11/642,963

(22) Filed: Dec. 21, 2006

(65) Prior Publication Data

US 2007/0144519 A1    Jun. 28, 2007

(30) Foreign Application Priority Data

Dec. 21, 2005 (AU) ............................. 2005907200

(51) Int. Cl.
*A61M 11/00* (2006.01)
(52) U.S. Cl. .................. 128/204.21; 128/204.18
(58) Field of Classification Search .............. 128/204.18
See application file for complete search history.

(56) References Cited

U.S. PATENT DOCUMENTS

| | | | | |
|---|---|---|---|---|
| 5,950,621 A | * | 9/1999 | Klockseth et al. | 128/204.26 |
| 6,035,851 A | * | 3/2000 | Wallen | 128/202.22 |
| 7,469,698 B1 | * | 12/2008 | Childers et al. | 128/204.23 |
| 2002/0174867 A1 | | 11/2002 | Gunaratnam | |
| 2004/0074495 A1 | | 4/2004 | Wickham | |
| 2004/0182386 A1 | | 9/2004 | Meier | |
| 2004/0210151 A1 | | 10/2004 | Tsukashima et al. | |
| 2010/0147301 A1 | | 6/2010 | Kwok | |

FOREIGN PATENT DOCUMENTS

| | | |
|---|---|---|
| DE | 4020522 | 1/1992 |
| EP | 1 516 641 | 3/2005 |
| EP | 1 579 884 | 9/2005 |
| WO | WO 2005/002655 | 1/2005 |

OTHER PUBLICATIONS

Kwok, U.S. Appl. No. 60/656,880, filed Mar. 1, 2005.
Kwok et al, U.S. Appl. No. 60/707,950, filed Aug. 15, 2006.
European Search Report for corresponding EP 06 12 6895, mailed Jun. 13, 2007, 6 pages.

* cited by examiner

*Primary Examiner* — Steven O Douglas
(74) *Attorney, Agent, or Firm* — Nixon & Vanderhye, PC

(57) ABSTRACT

Components of a CPAP or other patient ventilation apparatus have a remotely-readable identification tag encoded with component identification data. The flow generator controller 40 is programmed to receive data derived from the identification tag from a tag reader, and to adapt functions of the flow controller to coordinate with the component.

26 Claims, 6 Drawing Sheets

US 7,913,689 B2

IDENTIFICATION SYSTEM AND METHOD FOR MASK AND VENTILATOR COMPONENTS

CROSS REFERENCE TO PRIORITY APPLICATION

This application claims the benefit of Australian Application No. 2005907200, filed Dec. 21, 2005, incorporated herein by reference in its entirety.

BACKGROUND OF THE INVENTION

1. Field of the Invention

The present invention relates to an apparatus that delivers breathable gas to a patient, and to methods for coordinating breathable gas delivery to ventilator system components being used.

2. Description of Related Art

Apparatus to deliver breathable gas to a patient typically includes a flow generator, an air delivery conduit, and a patient interface. Prior to use, operating parameters of the flow generator, e.g., treatment pressure, need to be manually adjusted by the patient to coordinate with the peripheral components, e.g., patient interface, being used. For example, known flow generators include a menu system that allows the patient to select the type of peripheral components being used, e.g., by brand, method of delivery, etc. Once the components are selected by the patient, the flow generator can select appropriate operating parameters of the flow generator that best coordinate with the selected components.

One limitation of the menu set up system is a lack of future mask compatibility. The flow generator is programmed on initial set up to recognise a number of mask types and to compensate for their known pressure-flow characteristics. However the flow generator does not recognise newer mask types, and these are selected by closest fit to the existing selection options.

As a result, the design of new masks and other ventilator system components is limited by the need to keep similar pressure-flow characteristics to a known mask or component type, and new technologies which have significantly different pressure-flow characteristics—or which have variability in characteristics—have not previously been able to be adopted due to non-compatibility with the flow generators.

The present invention provides improvements to known apparatus to facilitate the coordination between the flow generator and the CPAP apparatus components.

The present invention further provides methods for coordinating the flow generator and the CPAP apparatus components.

SUMMARY OF THE INVENTION

In one form, the invention provides a CPAP apparatus comprising:
  a flow generator that generates a supply of pressurized air, said flow generator including a programmable controller;
  one or more CPAP apparatus components having a remotely-readable identification tag containing identification data;
  wherein said controller includes a data input adapted to receive data derived from a remote identification tag reader which reads said identification data, and is further adapted to adjust one or more functions of the flow generator in response to said received data.

A further form of the invention provides apparatus for set-up of a CPAP treatment parameters for a patient, including:
  a CPAP apparatus according to the invention;
  a remote identification tag reader for reading the component tag; and
  a data communication path for communicating data derived from the tag to the flow generator controller.

A further form of the invention provides a method of setting up CPAP treatment parameters for a flow generator of CPAP apparatus according to the invention, including the steps of:
  transporting the flow generator to a location, said location having a remote identification tag reader for reading a remote identification tag of a CPAP apparatus component;
  reading said remote identification tag of a CPAP apparatus component for use with the flow generator;
  deriving data from said tag and communicating said data to the flow generator controller to adapt the flow generator for use with said component.

Further aspects of the invention are set out in the claims.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

Further preferred embodiments of the invention will now be described with reference to the accompanying drawings, in which.

DETAILED DESCRIPTION OF PREFERRED EMBODIMENTS

Figure 1:
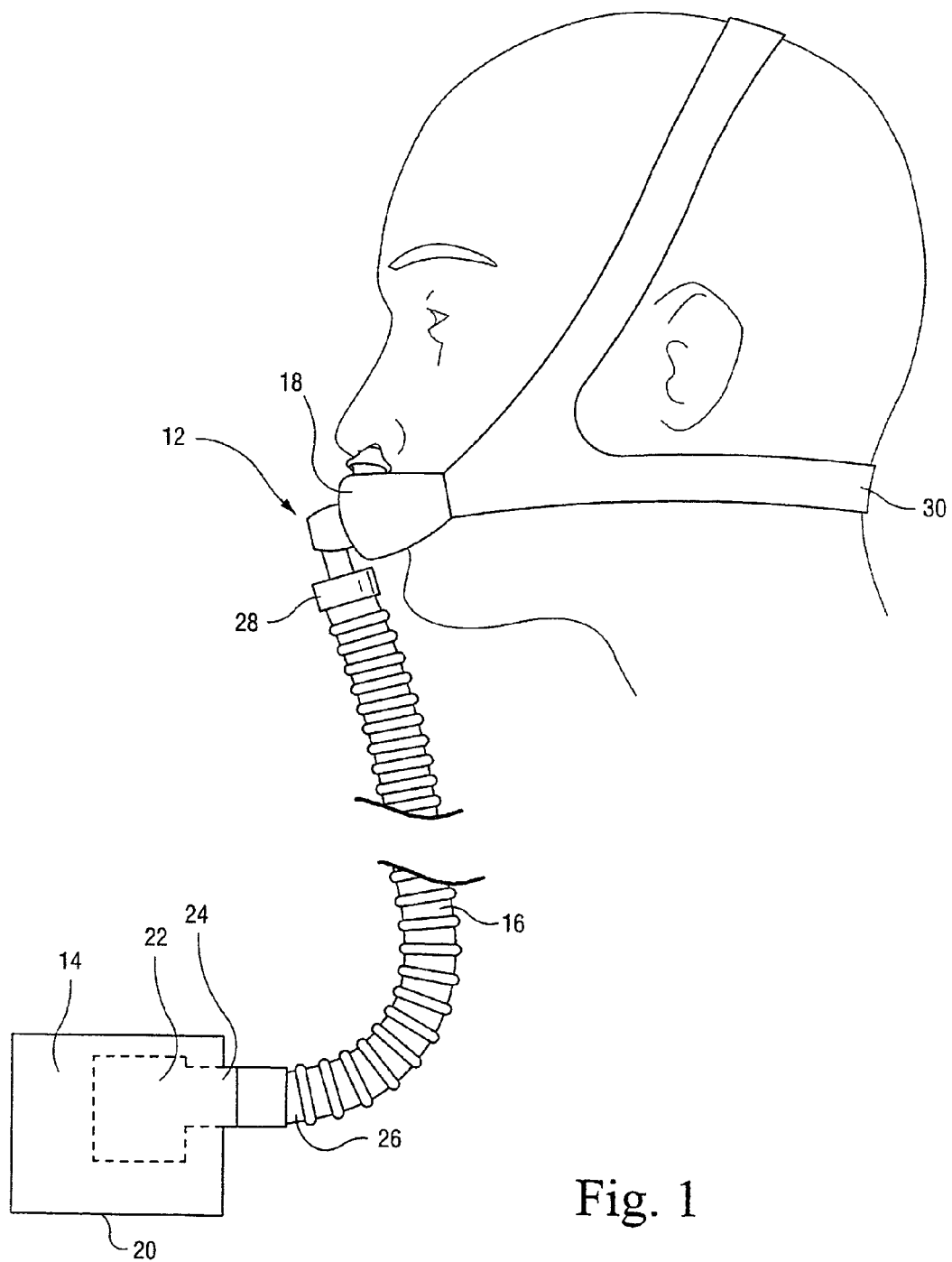
FIG. 1 is a schematic side view of an embodiment of an apparatus that delivers breathable gas to a patient.
Figure 2:
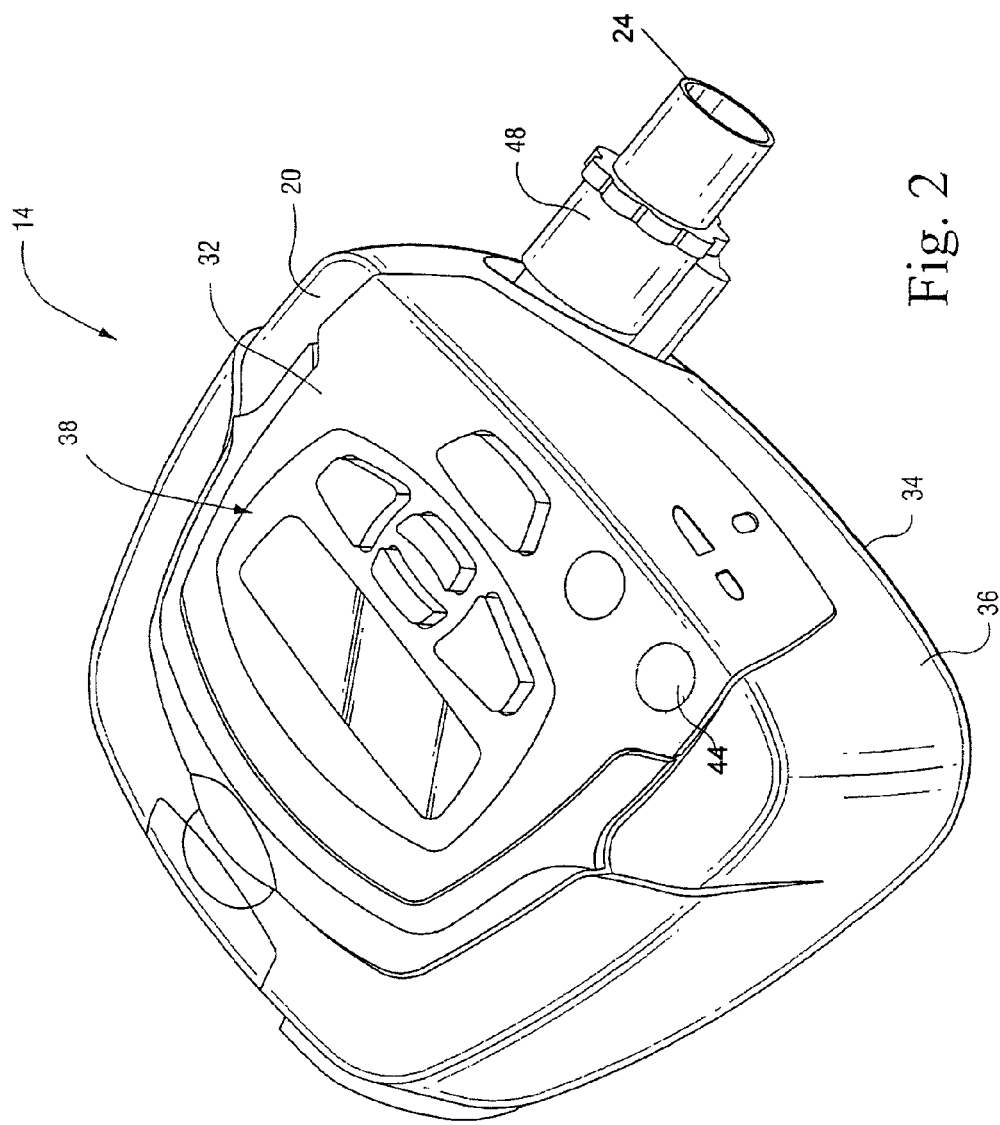
FIG. 2 is a top perspective view illustrating a flow generator.

FIGS. 1 and 2 illustrate an apparatus 12 that delivers a supply of pressurized breathable air to a patient for treatment, e.g., of Sleep Disordered Breathing (SDB) with CPAP or Non-Invasive Positive Pressure Ventilation (NIPPV). As best shown in FIG. 1, the apparatus 12 generally includes a flow generator 14, an air delivery conduit 16, and a patient interface 18.

The flow generator 14 is structured to generate a supply of pressurized air to be provided to a patient for treatment. The flow generator 14 includes a housing 20 and a blower 22 supported within the housing 20. As is known in the art, the blower 22 is operable to draw a supply of air into the housing 20 through one or more intake openings and provide a pressurized flow of air at an outlet 24.

The supply of pressurized air is delivered to the patient via the air delivery conduit 16 that includes one end 26 coupled to the outlet 24 of the flow generator 14 and an opposite end 28 coupled to the patient interface 18, as shown in FIG. 1.

The patient interface 18 comfortably engages the patient's face and provides a seal. The patient interface 18 may have any suitable configuration as is known in the art, e.g., full-face mask, nasal mask, oro-nasal mask, mouth mask, nasal prongs, etc. Also, any suitable headgear arrangement 30 may be utilized to comfortably support the patient interface 18 in a desired position on the patient's face.

FIG. 2 shows an example of a flow generator unit.

As shown in FIG. 2, the housing 20 of the flow generator 14 includes an upper wall 32, a lower wall 34, and side walls 36 that interconnect the upper and lower walls 32, 34. In the illustrated embodiment, the outlet 24 is provided in one of the side walls 36, optionally as part of a conduit connection adaptor 48. Also, the upper wall 32 incorporates a manual control unit 38 for adjusting one or more parameters of the flow generator 14, e.g., treatment pressure. However, the outlet 24 and/or control unit 38 may be incorporated into any of the walls of the housing 20. Also, it should be understood that the flow generator 14 may include additional features incorporated into the housing 20, e.g., power supply.

Figure 3:
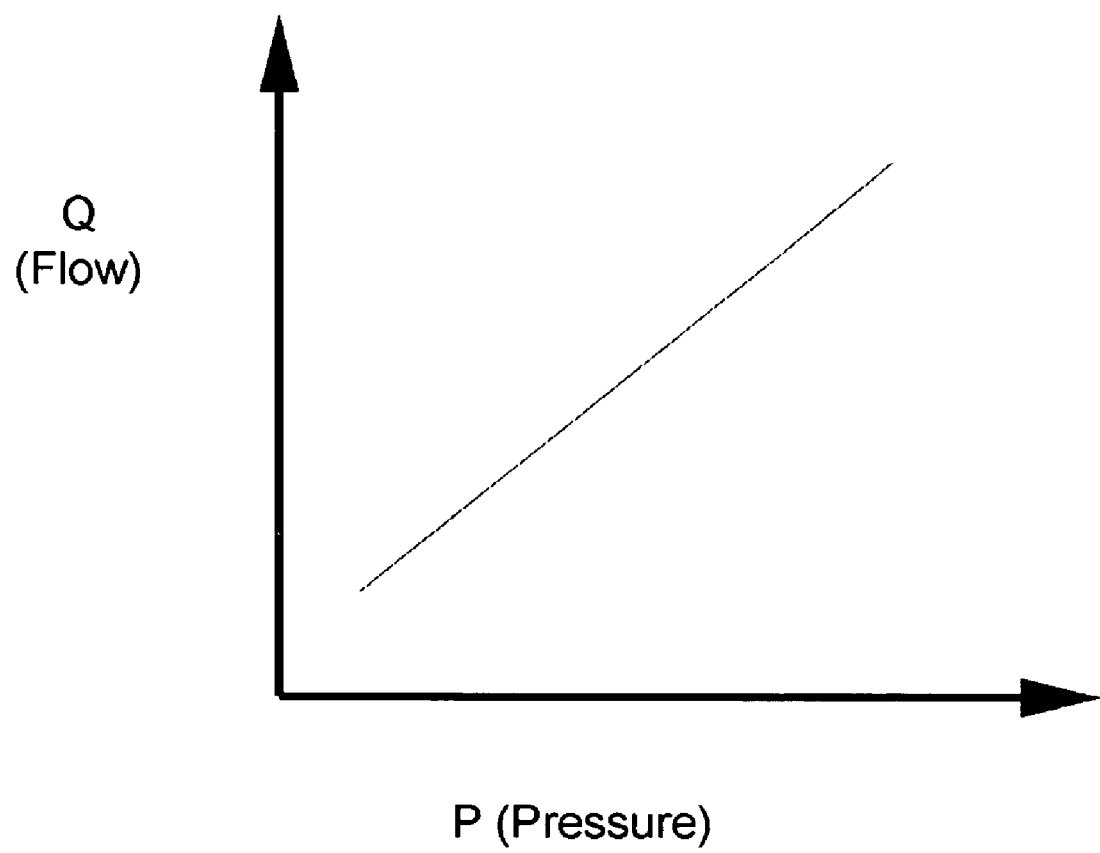
FIG. 3 is an example of a pressure-flow curve for a patient mask.

FIG. 3 shows an example of a pressure-flow curve for a patient interface, for example as may be measured in production testing of the interface.

The measured pressure-flow characteristics of interface may be stored as data in a radio frequency identification (RFID) chip incorporated in the interface. For example, the component identification data in the chip may include values for gradient and y-intercept coefficients for a line of best fit to the curve, or values of coefficients for polynomial or logarithmic approximations to the curve.

Figure 4:
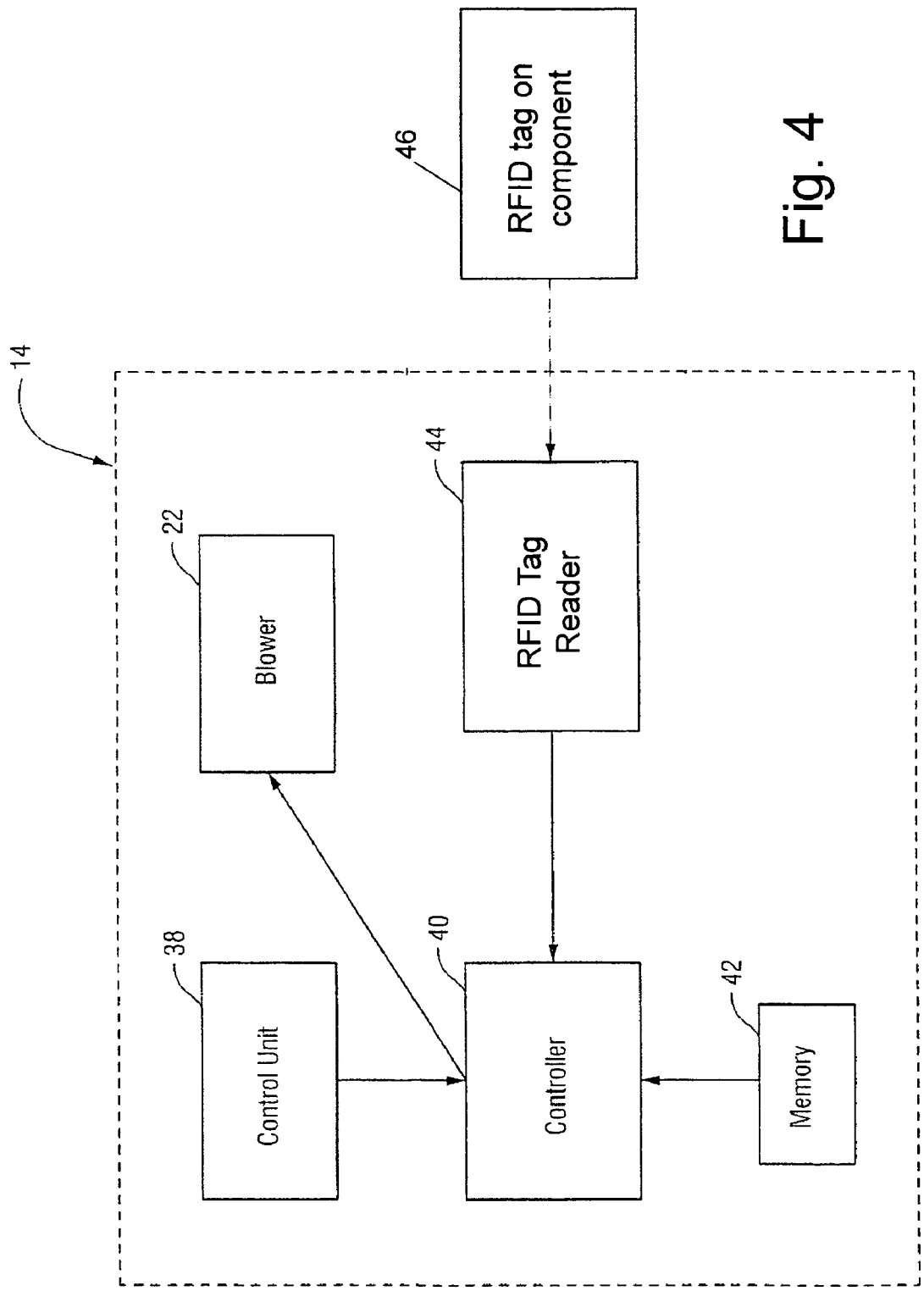
FIG. 4 is a block diagram of a flow generator set-up apparatus according to an embodiment of the invention, having an internal tag reader.

As shown schematically in FIG. 4, the flow generator 14 includes a controller 40 operable to receive input signals and to control operation of the blower 22 based on input signals. Input signals may be provided by the control unit 38 which has a plurality of control features that can be manually selected by the patient to adjust various parameters of the flow generator 14. For example, the patient may select the type of patient interface 18 being used, e.g., via a menu system of the control unit 38, from a number of known patient interface types so that the controller 40 can adjust the blower outlet pressure so that it coordinates with the selected patient interface 18. The controller 40 may include a memory 42 that stores preferred operating parameters for a variety of patient interfaces, e.g., by brand or method of delivery. When the controller 40 receives the input signal regarding the selected patient interface 18 from the control unit 38, the controller 40 can operate the blower 22 based on the stored operating parameters in the memory 42 for the selected patient interface 18. Alternatively, the preferred operating parameters for a selected patient interface 18 may be entered manually through the control unit 38.

As also shown in FIG. 4, the controller 40 of the flow generator 14 is adapted to receive data derived from remote reading of a identification tag 46 attached to or incorporated into one or more of the peripheral components, and to select appropriate operating parameters of the flow generator 14 to coordinate with the selected peripheral components.

In one embodiment, the remotely readable identification tag may be a radio frequency identification (RFID) tag, having either read-only or read-and-write capabilities depending on the type of tag reader 44 with which the tag is to be used and the functionalities desired.

The tag stores identification data for the component, including for example a unique identifier such as serial number, a batch number, component type and/or size, and optionally component performance parameters such as pressure-flow performance parameters of the component measured during post-production testing of the component.

Other types of remote-reading technologies which may be employed in the present invention include bar coding, powerless piezo, infrared, optical recognition of colour and/or shape, smartcard and EPROM (erasable programmable read-only memory). Alternatively, the component may be tagged with a code which may be entered into the flow generator control unit 38 or otherwise communicated to the processor, and then used to retrieve the detailed information from a remote database using telecommunications, for example short message service or internet protocol form via a wired or wireless modem. The database may also be located within the flow generator and may be updated with software upgrades.

The tag reader 44 may be integrated with the flow generator unit as shown in FIG. 4, for example formed on a surface of the flow generator casing (see FIG. 2), or may be separate from the flow generator and include means for communicating with the flow generator controller 40 via a USB, network, modem or other communications port in the casing.

In use, the tagged component is swiped over or otherwise placed in sufficient proximity to the tag reader 44 to allow detection of the identification data, which data is then communicated from the reader to the controller 40. The controller 40 in turn uses this data to adjust one or more functions of the flow generator.

In one embodiment of the invention, the identification data includes pressure-flow performance parameters for a component in the airflow path, such as a filter, conduit or patient interface, and the controller adjusts the pressure and/or flow characteristics of the blower in response to the data.

In another embodiment, the identification data includes identity data for a component, and the controller 40 records the flow generator operation time against the component identity to cause a warning message to be displayed on the display of the control unit 38 advising the patient to replace the component after a set operation time or a set period has elapsed.

By way of example, the controller 40 may receive and store the identity data for an antibacterial filter of the type used in CPAP or other ventilatory therapy in hospitals, and display a warning message when the filter is due for replacement. Continued use of the component after its safe usage time has elapsed may cause the controller to shut down operation of the blower.

In a further example, the controller 40 may also use the identification data to cause to be displayed on the control unit 38 display the component type, size or settings, to facilitate reordering of components or for clinician or service review.

Other flow generator functions which may be controlled in response to detection of the component identification data include:

- To limit the function of the flow generator to a single session where the identification data identifies the component as being adapted only for a single use;
- Where a patient data code is available in a format recognisable to the controller or in machine-readable format, to limit the use of the component to the particular patient for hygiene purposes, for example by scanning barcodes on both the patient data and on the component and preventing the flow generator from operating with that component for any other patient code;
- To switch on additional functionalities of the flow generator where it is detected that the component is suitable for that functionality, or for a limited trial period where a new component is detected.

In one embodiment, discussed below with reference to FIGS. 5 and 6, tag readers are external to the flow generators and are located at clinics and at suppliers of CPAP components such as patient interfaces.

Figure 5:
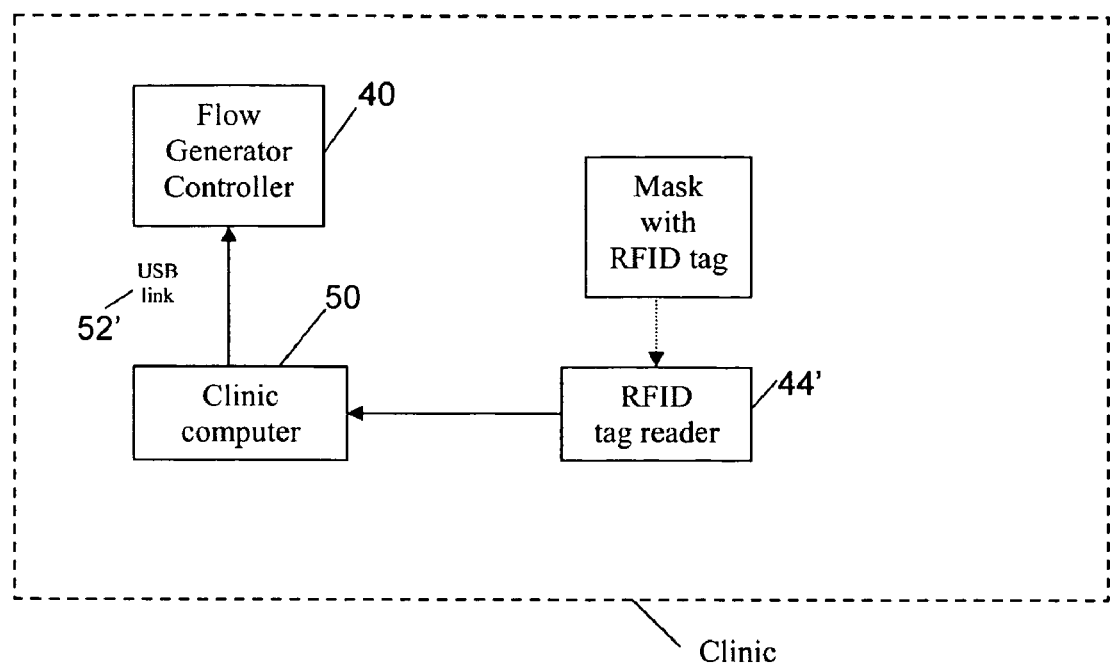
FIG. 5 is a block diagram of a further embodiment of the invention, where the tag reader is separate from the flow generator.

As shown in FIG. 5, a clinic or other central location has a tag reader 44' connected to one or more computers 50. The computer 50 has a communications link 52'—such as a USB, network, wireless network or modem—for communication with the flow generator controller via a compatible communications device in the flow generator.

Figure 6:
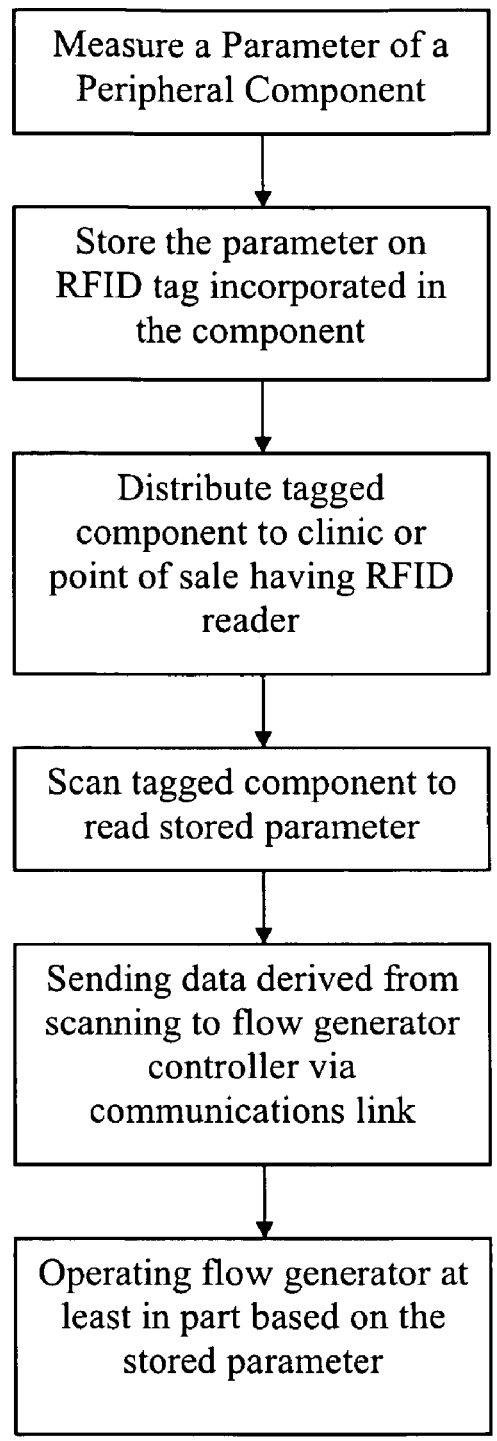
FIG. 6 is a flowchart of a method using the apparatus of FIG. 5.

As shown in FIG. 6, the performance characteristics of a component such as a patient interface are tested on the production line, and the performance parameters form part of the identification data recorded onto an RFID or other readable chip which is incorporated into the component.

The patient brings the flow generator on his/her visit to the clinic. At the clinic, the clinician assesses the patient and helps the patient select the correct patient interface and other components for use with the flow generator. The clinician also determines the desired treatment settings for the patient and programs the flow generator controller to those settings. Programming of the flow generator may be done using the menu of the control unit 38 or via a communications link 52.

The tagged component is swiped past the tag reader 44', which reads the identification data from the component tag. The data is then communicated to the computer 50, which displays relevant component data on the computer display and communicates information about the component to the flow generator controller.

In the embodiment of FIG. 6, all or a selected portion of the component identification data is relayed from the computer 50 to the controller 40, with the flow generator controller programmed to receive that data and calculate adjustments for operating parameters of the flow generator to coordinate with the properties of the component.

In an alternative embodiment, the computer 50 is programmed to process the component identification data received from the tag reader to derive instructions sent to the controller 40 for adjustment of the flow generator operating parameters.

In a further alternative embodiment, a CPAP apparatus component such as a patient interface has a readable/writable tag which is capable of storing data written to it from the flow generator. The data to be written to the component tag may include treatment history data indicative of treatment performance and efficacy and patient compliance, to be uploaded to the patient interface either regularly or prior to a patient visit to the clinic. In this way, the patient may simply take the mask or other patient interface with him or her on a visit to the clinician, instead of needing to take the much larger and heavier flow generator. The clinician may then interrogate the treatment history data in the mask tag via a tag reader at the clinic, and after review the patient's treatment may write back to the tag with instructions for ongoing treatment. On return from the clinic, or prior to the next treatment session, these instructions may then be downloaded to the flow generator via its tag reader and the programming of the flow generator settings adjusted accordingly.

In a yet further embodiment, the component forms part of an airflow pathway comprising a humidifier, conduit and the patient interface, and the component identification may comprise a remote identification as discussed above or physical or other connection, for example by magnetic reed switch or other means as discussed in U.S. patent application Nos. 60/656,880 filed 1 Mar. 2005 (Kwok) and 60/707950 filed 15 Aug. 2005 (Kwok, Gregory, Selvarajan), the contents of which are incorporated herein by reference.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. A breathable pressurized gas delivery apparatus comprising:
   a flow generator that generates a supply of pressurized gas, said flow generator including a programmable controller; and
   one or more breathable pressurized gas delivery apparatus components having a remotely-readable identification tag containing identification data, the identification data including operational data for operating the breathable pressurized gas delivery apparatus,
   wherein said controller includes a data input set to receive data derived from an identification tag reader which reads said identification data, and is further set to adjust at least one therapy related parameter of the flow generator to coordinate with said at least one breathable pressurized gas delivery apparatus component in response to said received data.

2. An apparatus according to claim 1, wherein said component is a component in an air flow path.

3. An apparatus according to claim 2, wherein the identification data includes indication of air flow characteristics of the component.

4. An apparatus according to claim 3, wherein said identification data includes indication of pressure-flow characteristics of the component.

5. An apparatus according to claim 4, wherein said pressure-flow characteristics are indicative of pressure-flow curve characteristics of the component.

6. An apparatus according to claim 4, wherein said air flow path comprises humidifier, air conduit, and patient interface components.

7. An apparatus according to claim 5, wherein said component is a patient interface and the pressure-flow characteristics are the pressure-flow characteristics of a patient interface and the pressure-flow characteristics are the pressure-flow characteristics of a patient interface type of which the patient interface is a member.

8. An apparatus according to claim 6, wherein said pressure-flow characteristics are indicated by reference to the patient interface type.

9. An apparatus according to claim 4, wherein said pressure-flow characteristics are measured pressure-flow characteristics of the individual patient interface.

10. An apparatus according to claim 1, wherein said remotely-readable tag is selected from the group comprising radio frequency identification (RFID), barcoding, powerless piezo, infrared, smartcard, EPROM memory, or shape or colour of a part or whole of the component.

11. Apparatus for set-up of breathable pressurized gas delivery treatment parameters for a patient, including:
  a breathable pressurized gas delivery apparatus according to claim 1;
  a remote identification tag reader for reading the component tag; and
  a data communication path for communicating data derived from the tag to the flow generator controller.

12. Apparatus according to claim 11, wherein said tag reader is external to the flow generator and the data communication means includes a data input port on the flow generator.

13. Apparatus according to claim 12, further including a computer processor linked to the tag reader for communicating said data to the flow generator controller.

14. A method of setting up breathable pressurized gas delivery treatment parameters for a flow generator of a breathable pressurized gas delivery apparatus according to claim 1, the method comprising:
  reading a remote identification tag of a breathable pressurized gas delivery apparatus component for use with the flow generator, said remote identification tag including operational data for operating the breathable pressurized gas delivery apparatus:
  retrieving operational data from said tag and communicating said operational data to the flow generator controller; and
  configuring at least one therapy related parameter of the flow generator based in part on the operational data.

15. A method according to claim 14, wherein said component is a component in the air flow path.

16. A method according to claim 15, wherein said air flow path comprises humidifier, air conduit and patient interface components.

17. A method according to claim 14, wherein said component is a patient interface.

18. A method according to claim 14, wherein said location is a clinic or a supplier for said components.

19. A method according to claim 14, wherein said communication step includes establishing a computer communications path to said flow generator controller.

20. A method according to claim 19, wherein said communications path includes a universal serial bus (USB) link.

21. A breathable pressurized gas delivery apparatus comprising:
  a flow generator that generates a supply of pressurized gas, said flow generator including a programmable controller;
  an air flow path from the flow generator to a patient, said air flow path comprising a humidifier component, an air tube component, and a patient interface component; and
  one or more of said air flow path components having an identification device containing identification data including data on pressure-flow characteristics of the component,
  wherein said controller includes a data input adapted to receive data derived from an identification device reader which reads said identification data, and is further adapted to adjust one or more pressure flow characteristics of the flow generator in response to said received data.

22. Apparatus according to claim 21, wherein said identification device and identification device reader comprise a physical connection between the flow generator and the air pathway component.

23. Apparatus according to claim 21, wherein said identification device comprises a remotely-readable identification tag and said identification device reader comprises a remote identification tag reader.

24. A pressurized breathable gas delivery apparatus component comprising
  a tag that is configured to be remotely readable, wherein the tag includes treatment history data, patient compliance data, or for a pressurized breathable gas delivery device, wherein the breathable pressurized gas delivery apparatus component is set to coordinate with the pressurized breathable gas delivery device to adjust one or more functions of pressurized breathable gas delivery based at least in part on the treatment history data or patient compliance data.

25. Apparatus component according to claim 24, wherein the component is a patient interface.

26. The apparatus of claim 1, wherein the at least one therapy related parameter is a pressure and/or flow parameter.

* * * * *